(12) United States Patent
Flygare et al.

(10) Patent No.: US 10,286,183 B2
(45) Date of Patent: May 14, 2019

(54) STEERABLE SHEATH CATHETER AND METHODS OF USE

(71) Applicant: Merit Medical Systems, Inc., South Jordan, UT (US)

(72) Inventors: Mark Flygare, Farmington, UT (US); Richard D. Jenkins, Kennett Square, PA (US); Jon Jensen, South Ogden, UT (US); Gregory R. McArthur, Sandy, UT (US); Richard Paul Jenkins, Bluffdale, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 281 days.

(21) Appl. No.: 15/358,549

(22) Filed: Nov. 22, 2016

(65) Prior Publication Data

US 2017/0143940 A1 May 25, 2017

Related U.S. Application Data

(60) Provisional application No. 62/260,062, filed on Nov. 25, 2015.

(51) Int. Cl.
  *A61M 25/01* (2006.01)
  *A61M 25/09* (2006.01)
  *A61B 18/00* (2006.01)

(52) U.S. Cl.
  CPC .... *A61M 25/0133* (2013.01); *A61M 25/0136* (2013.01); *A61M 25/09041* (2013.01); *A61B 2018/00309* (2013.01); *A61M 25/0147* (2013.01); *A61M 2205/581* (2013.01); *A61M 2205/582* (2013.01)

(58) Field of Classification Search
  CPC ............... A61M 25/0147; A61M 25/0136
  See application file for complete search history.

(56) References Cited

U.S. PATENT DOCUMENTS

| | | |
|---|---|---|
| 2,393,002 A | 1/1946 | Larkin |
| 2,898,917 A | 8/1959 | Wallace |
| 3,225,762 A | 12/1965 | Guttman |
| 3,416,532 A | 12/1968 | Grossman |
| 3,610,231 A | 10/1971 | Takahashi et al. |
| 3,683,929 A | 8/1972 | Holter |

(Continued)

FOREIGN PATENT DOCUMENTS

| | | |
|---|---|---|
| RU | 2012371 | 5/1994 |
| RU | 2415682 | 4/2011 |

(Continued)

OTHER PUBLICATIONS

International Preliminary Report and Written Opinion dated Dec. 27, 2016 for PCT/US2015/038112.

(Continued)

*Primary Examiner* — Laura A Bouchelle
(74) *Attorney, Agent, or Firm* — Stoel Rives LLP

(57) ABSTRACT

A steerable sheath catheter for providing access into body vasculature, the catheter including a sheath handle with an actuator and a control mechanism operative to selectively deflect a tip section of the catheter, and a feedback mechanism that provides, for example, tactile feedback that is felt by the user as the control mechanism passes a neutral position while deflecting the tip section.

21 Claims, 13 Drawing Sheets

(56) References Cited

U.S. PATENT DOCUMENTS

| | | |
|---|---|---|
| 3,830,238 A | 8/1974 | Kurtz et al. |
| 3,863,641 A | 2/1975 | Popa |
| 3,867,945 A | 2/1975 | Long |
| 3,937,418 A | 2/1976 | Critelli |
| 3,943,929 A | 3/1976 | Patel |
| 4,068,383 A | 1/1978 | Krebs |
| 4,105,031 A | 8/1978 | Kurtz et al. |
| 4,202,510 A | 5/1980 | Stanish |
| 4,203,430 A | 5/1980 | Takahashi |
| 4,228,802 A | 10/1980 | Trott et al. |
| 4,439,189 A | 3/1984 | Sargeant et al. |
| 4,571,239 A | 2/1986 | Heyman |
| 4,580,551 A | 4/1986 | Siegmund et al. |
| 4,608,982 A | 9/1986 | Pollard |
| 4,692,154 A | 9/1987 | Singery et al. |
| 4,769,019 A | 9/1988 | Kerwin |
| 4,862,891 A | 9/1989 | Smith |
| 4,883,474 A | 11/1989 | Sheridan et al. |
| 4,920,980 A | 5/1990 | Jackowski |
| 5,026,358 A | 6/1991 | Everett et al. |
| 5,040,543 A | 8/1991 | Badera |
| 5,047,018 A | 9/1991 | Gay |
| 5,108,368 A | 4/1992 | Hammerslag et al. |
| 5,141,503 A | 8/1992 | Sewell |
| 5,157,813 A | 10/1992 | Carroll |
| 5,205,830 A | 4/1993 | Dassa et al. |
| 5,207,661 A | 5/1993 | Repschlager |
| 5,211,644 A | 5/1993 | Vanbeek et al. |
| 5,297,310 A | 3/1994 | Cox et al. |
| 5,300,050 A | 4/1994 | Everett et al. |
| 5,312,357 A | 5/1994 | Buijs |
| 5,364,351 A | 11/1994 | Heinzelman et al. |
| 5,370,610 A | 12/1994 | Reynolds et al. |
| 5,397,321 A | 3/1995 | Houser et al. |
| 5,409,462 A | 4/1995 | Ross |
| 5,409,468 A | 4/1995 | Sachse |
| 5,456,664 A | 10/1995 | Heinzelman et al. |
| 5,540,648 A | 7/1996 | Yoon et al. |
| 5,601,087 A | 2/1997 | Gunderson et al. |
| 5,616,131 A | 4/1997 | Sauer |
| 5,630,795 A | 5/1997 | Kuramoto et al. |
| 5,653,696 A | 8/1997 | Shiber et al. |
| 5,772,670 A | 6/1998 | Brosa |
| 5,807,341 A | 9/1998 | Heim et al. |
| 5,895,400 A | 4/1999 | Abela |
| 5,897,534 A | 4/1999 | Heim et al. |
| 5,987,344 A * | 11/1999 | West ............... A61N 1/0565 600/373 |
| 6,045,623 A | 4/2000 | Cannon et al. |
| 6,146,355 A | 11/2000 | Biggs |
| 6,171,277 B1 | 1/2001 | Ponzi |
| 6,183,450 B1 | 2/2001 | Lois |
| 6,193,691 B1 | 2/2001 | Beardsley |
| 6,254,581 B1 | 7/2001 | Scott |
| 6,468,260 B1 | 10/2002 | Bumbalough et al. |
| 6,500,167 B1 | 12/2002 | Webster |
| 6,514,273 B1 | 2/2003 | Voss et al. |
| 6,530,913 B1 | 3/2003 | Giba et al. |
| 6,530,935 B2 | 3/2003 | Wensel et al. |
| 6,638,253 B2 | 10/2003 | Breznock |
| 6,907,992 B2 | 6/2005 | McMichael et al. |
| 7,037,290 B2 | 5/2006 | Gardeski et al. |
| 7,407,128 B1 | 8/2008 | Chang |
| 7,497,854 B2 | 3/2009 | Gill et al. |
| 7,578,814 B2 | 8/2009 | Accisano et al. |
| 7,740,623 B2 | 6/2010 | Nayak et al. |
| 7,758,586 B2 | 7/2010 | Muto et al. |
| 8,220,460 B2 | 7/2012 | Tanaka |
| 8,246,752 B2 | 8/2012 | Boyle, Jr. |
| D669,168 S | 10/2012 | Krueger et al. |
| D669,577 S | 10/2012 | Holsinger |
| 8,388,759 B2 | 3/2013 | Boyle, Jr. et al. |
| 8,409,070 B2 | 4/2013 | Carol et al. |
| D700,322 S | 2/2014 | Kleiner |
| D708,741 S | 7/2014 | Harrison et al. |
| D710,495 S | 8/2014 | Wu et al. |
| 8,870,892 B2 | 10/2014 | Feng et al. |
| D718,440 S | 11/2014 | Besse et al. |
| D724,725 S | 3/2015 | Chang |
| 8,979,744 B2 | 3/2015 | Braga et al. |
| D726,304 S | 4/2015 | Yatabe et al. |
| D728,781 S | 5/2015 | Pierson et al. |
| D732,160 S | 6/2015 | Du |
| 9,604,033 B2 | 3/2017 | Lazarus |
| 9,649,415 B2 | 5/2017 | Lazarus |
| 9,821,097 B2 | 11/2017 | Lazarus |
| 2001/0005785 A1 | 6/2001 | Sachse |
| 2001/0007922 A1 | 7/2001 | Schwager |
| 2003/0208252 A1 | 11/2003 | O'Boyle et al. |
| 2003/0225364 A1 | 12/2003 | Kraft et al. |
| 2003/0236493 A1 | 12/2003 | Mauch |
| 2004/0035017 A1 | 2/2004 | Yang |
| 2004/0059293 A1 | 3/2004 | Chu et al. |
| 2004/0116852 A1 | 6/2004 | Scopton |
| 2004/0143197 A1 | 7/2004 | Soukup et al. |
| 2005/0131393 A1 | 6/2005 | Chu |
| 2005/0184186 A1 | 8/2005 | Tsoi et al. |
| 2005/0277875 A1 | 12/2005 | Selkee |
| 2006/0069311 A1 | 3/2006 | Sullivan |
| 2006/0142695 A1 | 6/2006 | Knudson |
| 2006/0173449 A1 | 8/2006 | Sharareh et al. |
| 2006/0217667 A1 | 9/2006 | Accisano et al. |
| 2006/0264925 A1 | 11/2006 | Sharareh et al. |
| 2006/0264988 A1 | 11/2006 | Boyle |
| 2006/0280773 A1 | 12/2006 | Roschak et al. |
| 2007/0016133 A1 | 1/2007 | Pepper |
| 2007/0060997 A1 | 3/2007 | de Boer |
| 2007/0078455 A1 | 4/2007 | Rashidi |
| 2007/0156116 A1 | 7/2007 | Gonzalez |
| 2007/0167923 A1 | 7/2007 | Deal |
| 2007/0287993 A1 | 12/2007 | Hinman et al. |
| 2008/0021415 A1 | 1/2008 | Durkin et al. |
| 2008/0236209 A1 | 1/2008 | Conti |
| 2008/0045921 A1 | 2/2008 | Anderson et al. |
| 2008/0097293 A1 | 4/2008 | Chin |
| 2008/0125848 A1 | 5/2008 | Kusleika et al. |
| 2008/0214948 A1 | 9/2008 | Myklebust et al. |
| 2008/0300462 A1 | 12/2008 | Intoccia et al. |
| 2009/0005771 A1 | 1/2009 | Lieber et al. |
| 2009/0012365 A1 | 1/2009 | Ueno et al. |
| 2009/0062769 A1 | 3/2009 | Graves |
| 2009/0227900 A1 | 9/2009 | Kim |
| 2009/0270800 A1 | 10/2009 | Spurchise et al. |
| 2009/0270838 A1 | 10/2009 | Berthiaume |
| 2009/0299327 A1 | 12/2009 | Tilson et al. |
| 2010/0070024 A1 | 3/2010 | Venturelli et al. |
| 2010/0101061 A1 | 4/2010 | Ha |
| 2010/0137775 A1 | 6/2010 | Hu et al. |
| 2010/0145368 A1 | 6/2010 | Chu et al. |
| 2010/0168731 A1 | 7/2010 | Wu et al. |
| 2010/0191057 A1 | 7/2010 | Jansen et al. |
| 2010/0222664 A1 | 9/2010 | Lemon |
| 2010/0234799 A1 | 9/2010 | Paris et al. |
| 2010/0249490 A1 | 9/2010 | Farnan |
| 2010/0249520 A1 | 9/2010 | Shelton, IV et al. |
| 2010/0264244 A1 | 10/2010 | Spencer |
| 2011/0040285 A1 | 2/2011 | Boyle |
| 2011/0062268 A1 | 3/2011 | Cheng |
| 2011/0077498 A1 | 3/2011 | McDaniel |
| 2011/0197888 A1 | 8/2011 | Deutsch et al. |
| 2011/0213300 A1 | 9/2011 | McWeeney et al. |
| 2011/0224647 A1 | 9/2011 | Lazarus |
| 2011/0264089 A1 | 10/2011 | Zirkle et al. |
| 2011/0282153 A1 | 11/2011 | Ueki |
| 2012/0116161 A1 | 5/2012 | Ueki |
| 2012/0157921 A1 | 6/2012 | Hoofnagle |
| 2012/0172703 A1 | 7/2012 | Esguerra et al. |
| 2013/0023840 A1 | 1/2013 | Loske et al. |
| 2013/0046250 A1 | 2/2013 | Bode |
| 2013/0158379 A1 | 6/2013 | Selkee |
| 2013/0184642 A1 | 7/2013 | O'Donnell et al. |
| 2013/0204087 A1 | 8/2013 | Jaworek et al. |
| 2013/0211385 A1 | 8/2013 | Lazarus |
| 2013/0253505 A1 | 9/2013 | Schultz |

(56) References Cited

U.S. PATENT DOCUMENTS

| | | | |
|---|---|---|---|
| 2013/0276718 A1 | 10/2013 | Valadez et al. | |
| 2013/0310767 A1 | 11/2013 | Solar | |
| 2014/0150782 A1 | 6/2014 | Vazales et al. | |
| 2014/0193138 A1 | 7/2014 | Koren | |
| 2014/0290014 A1 | 10/2014 | Myrick | |
| 2015/0148595 A1 | 5/2015 | Bagwell et al. | |
| 2015/0157399 A1 | 6/2015 | Romoscanu | |
| 2015/0335861 A1* | 11/2015 | Osypka | A61M 25/0147 604/95.04 |
| 2015/0374889 A1 | 12/2015 | Lazarus | |
| 2015/0374959 A1 | 12/2015 | Lazarus | |
| 2017/0050041 A1 | 2/2017 | Cosman | |
| 2017/0143940 A1 | 5/2017 | Flygare et al. | |

FOREIGN PATENT DOCUMENTS

| | | |
|---|---|---|
| WO | 199325264 | 12/1993 |
| WO | 199952481 | 10/1999 |

OTHER PUBLICATIONS

International Search Report and Written Opinion dated Aug. 27, 2015 for PCT/US2015/038086.
International Search Report and Written Opinion dated Oct. 1, 2015 for PCT/US2015/038112.
International Search Report dated Sep. 3, 2015 for PCT/US2015/038102.
Office Action dated May 11, 2017 for U.S. Appl. No. 14/318,571.
Office Action dated Sep. 12, 2017 for U.S. Appl. No. 14/318,571.
Office Action dated Nov. 3, 2017 for U.S. Appl. No. 13/840,986.
Office Action dated Dec. 7, 2012 for U.S. Appl. No. 13/045,274.
Catheter Prevents Clogging, Research & Development <http://www.rdmag.com-printpdf/award-winners/2011/08/catheter-prevents-clogging> ,Aug. 14, 2011 ,3 pages.
Express Dry Seal Chest Drain, Instructions for Use, Atruim www.atriummed.com ,2003 ,2 pgs.
Medical Plueroscopy, Cancer Treatment Centers of America , retrieved Aug. 19, 2013 <hhtp://www.cancercenter.com/treatments/medical-pleuroscopy/> ,Aug. 19, 2013 ,2 pages.
Occlutech Steerable Guiding Sheath, 2015.
Rocket® Cardiothoracic Range, Rocketmedical, Issue 1, R89947 ,Jan. 2011 ,23 pages.
Ben-Isaac, et al., Flexible Fiberoptic Pleuroscopy: Pleural and Lung Biopsy, Experimental Approaches, Chest Journal No. 67, <http://www.rdmag.com/printpdf/award-winners-2011/08/catheter-prevents-clogging> ,May 5, 1975 ,573-576.
Office Action dated Jun. 14, 2018 for U.S. Appl. No. 13/840,986.
International Search Report and Written Opinion dated Mar. 8, 2017 for PCT/US2016/063251.

* cited by examiner

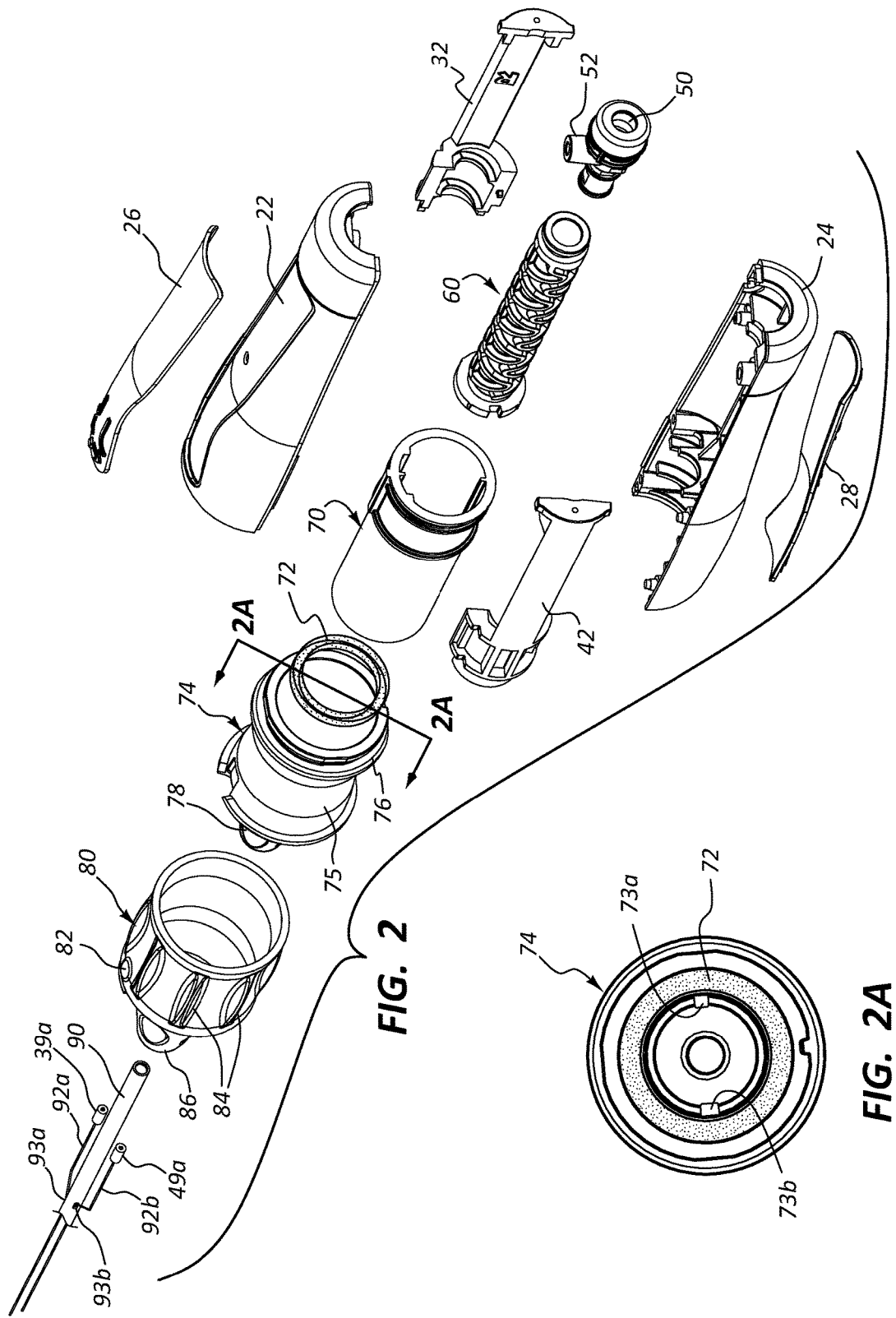

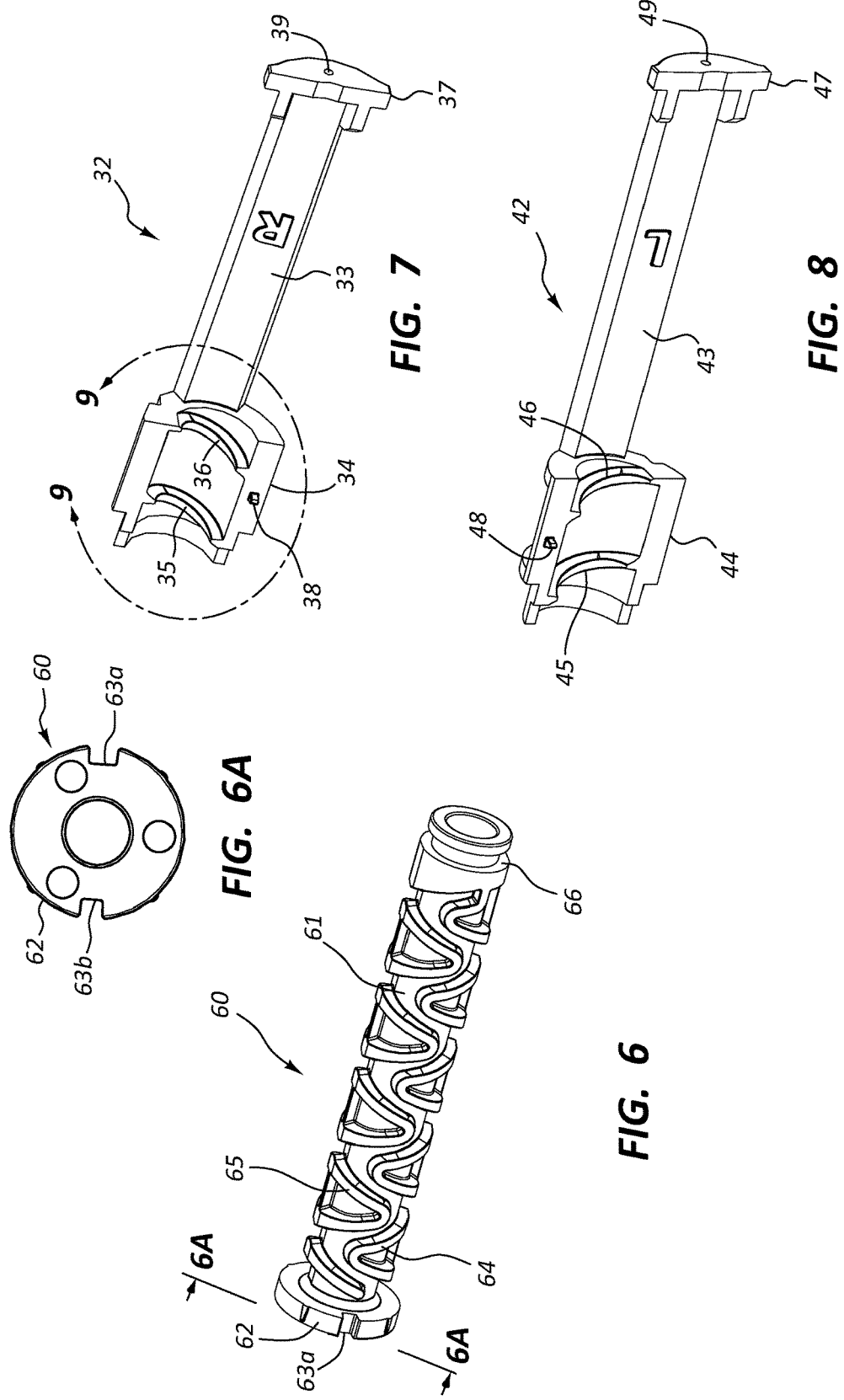

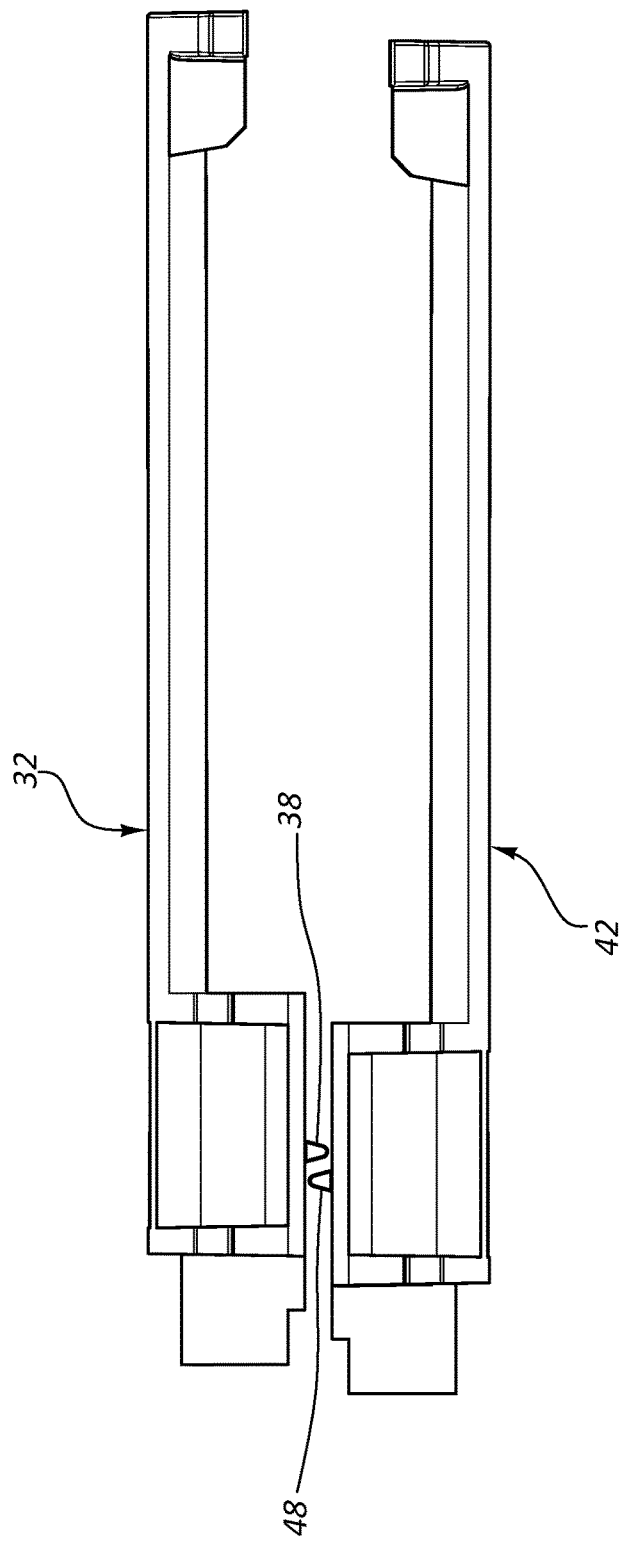

STEERABLE SHEATH CATHETER AND METHODS OF USE

CROSS REFERENCE TO RELATED APPLICATIONS

This application claims the benefit of U.S. Provisional Patent Application Ser. No. 62/260,062, filed Nov. 25, 2015, entitled "Steerable Sheath Catheter and Methods of Use," with its accompanying appendices, the disclosure of each of which is incorporated herein by this reference in its entirety.

TECHNICAL FIELD

The field of the present disclosure relates generally to medical devices. More specifically, the present disclosure relates to catheters which are used to provide access into the body or even more particularly, steerable sheath catheters which are used to provide access into body vasculature for introduction/delivery of additional tools, instruments, medications or fluids.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

FIG. 2 is an exploded view of the steerable sheath catheter of FIG. 1.

FIG. 2A is a plan view showing internals of the front knob section of the sheath handle of FIG. 2, on an enlarged scale.

FIG. 6 is an isometric view of the threaded rod or drive tube of the sheath handle of FIGS. 1-2.

FIG. 6A is a front plan view of the threaded drive tube of FIG. 6, on an enlarged scale.

FIG. 7 is an isometric view of the right guide (wire actuator).

FIG. 8 is an isometric view of the left guide (wire actuator).

FIG. 10 is a diagrammatic top view of the right and left guides of FIGS. 7-8 in position showing as when assembled in operation, on an enlarged scale.

DETAILED DESCRIPTION

Figure 1:
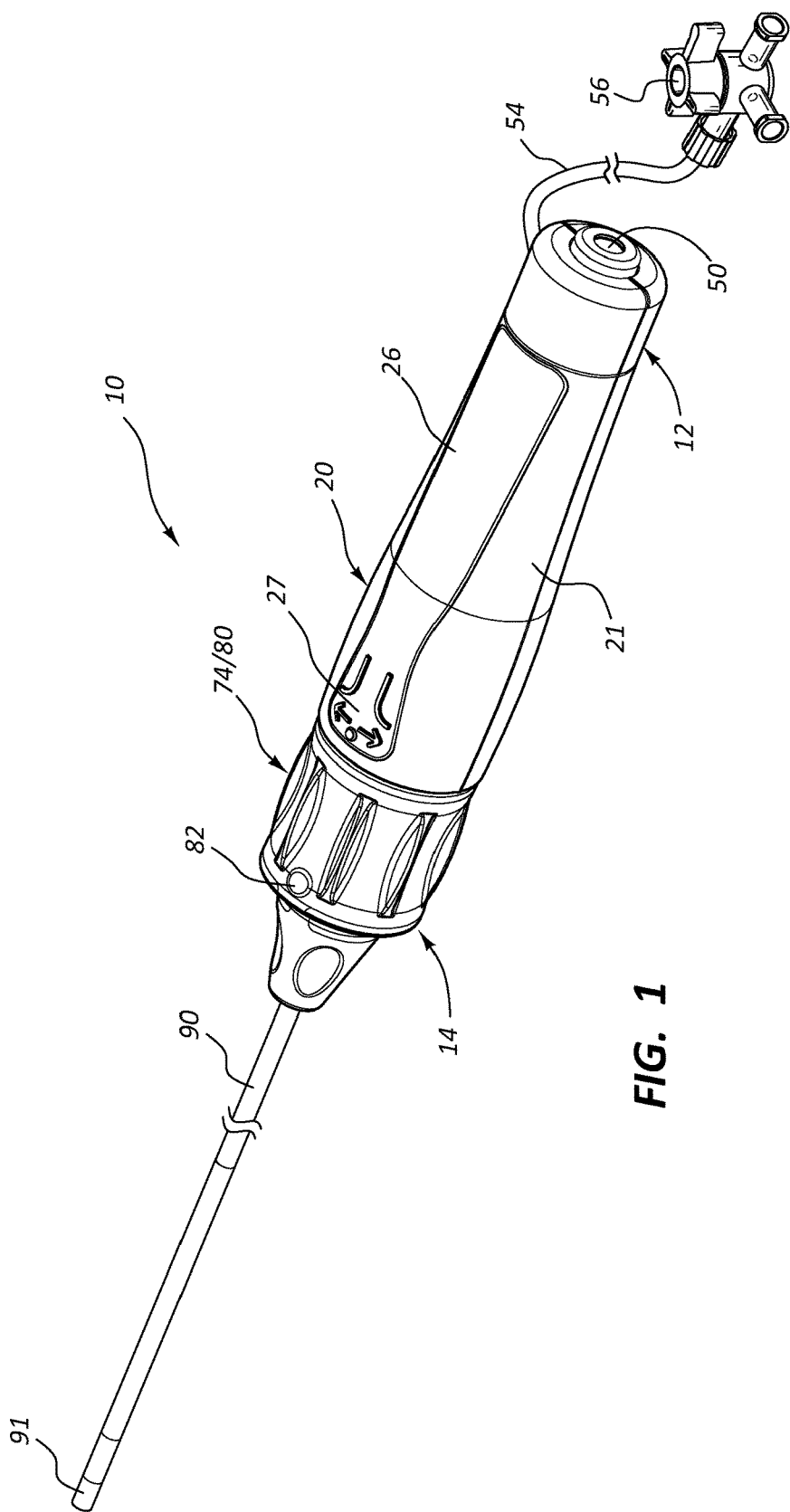
FIG. 1 is a top isometric view and FIG. 1A is a bottom isometric view of a steerable sheath catheter according to a first embodiment.

From the following descriptions, it should be understood that components of the embodiments as generally described and illustrated in the figures herein could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to" and "coupled to" refer to any form of interaction between two or more entities, including mechanical, electrical, magnetic, electromagnetic, fluid, and thermal interaction. Two components may be connected or coupled to each other even though they are not in direct contact with each other. For example, two components may be coupled to each other through an intermediate component.

The directional terms "proximal" and "distal" are used herein to refer to opposite locations on a medical device. The proximal end of the device is defined as the end of the device closest to the practitioner when the device is in use by the practitioner. The distal end is the end opposite the proximal end, along the longitudinal direction of the device, or the end furthest from the practitioner.

Certain embodiments described herein are directed to a steerable sheath for use with catheters to be positioned in a passageway leading to a body cavity for observation or for introduction/delivery of additional tools, instruments, medications or fluids.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

Referring in general to the following description and accompanying drawings, various embodiments of the present disclosure are illustrated to show its structure and method of operation. Common elements of the illustrated embodiments may be designated with similar reference numerals. Accordingly, the relevant descriptions of such features apply equally to the features and related components among all the drawings. Any suitable combination of the features, and variations of the same, described with components illustrated in FIG. 1, can be employed with the components of FIG. 2, and vice versa. This pattern of disclosure applies equally to further embodiments depicted in subsequent figures and described hereinafter. It should be understood that the figures presented are not meant to be illustrative of actual views of any particular portion of the actual structure or method, but are merely idealized representations employed to more clearly and fully depict the present invention defined by the claims below.

Figure 1A:
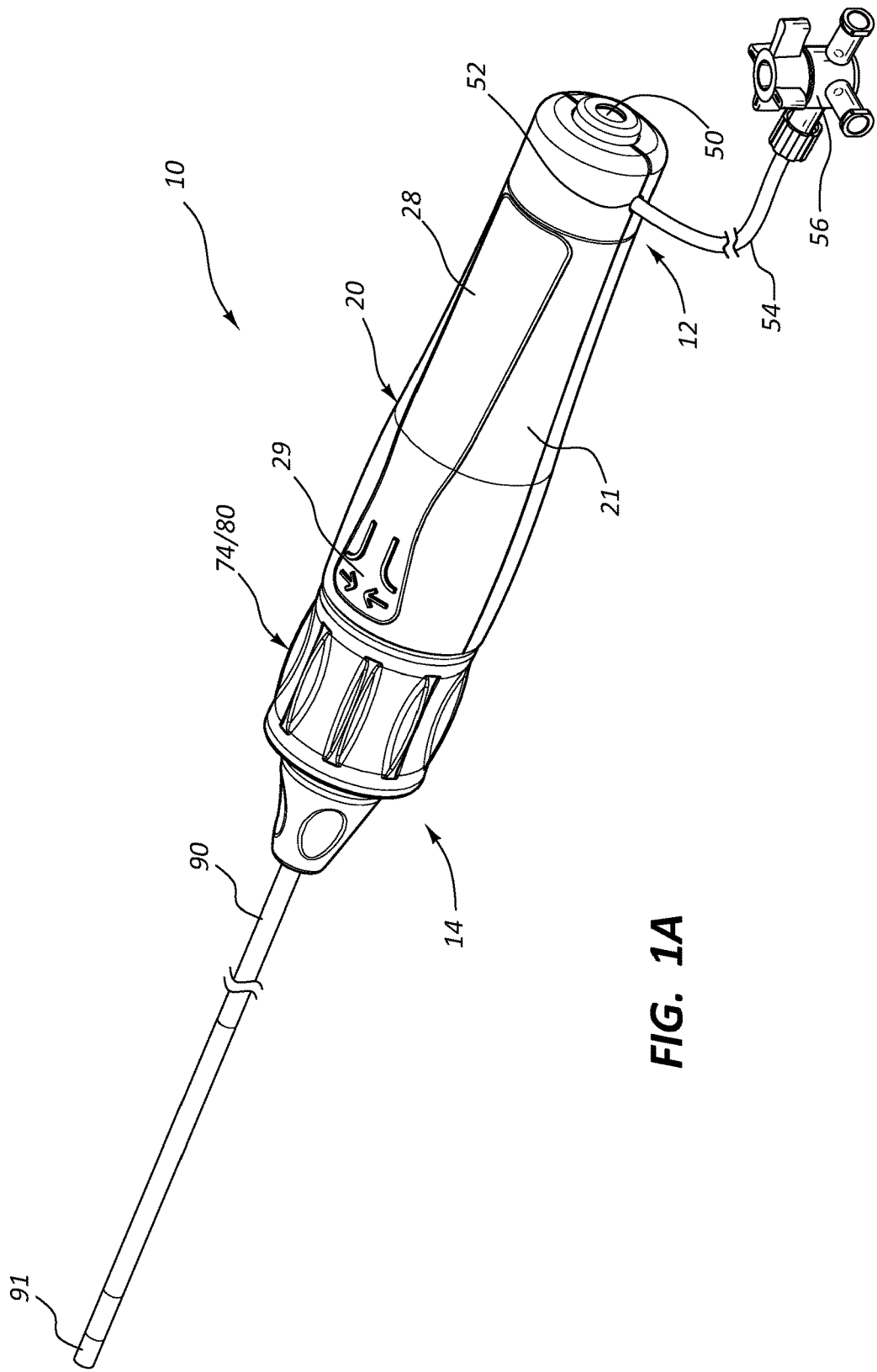

FIG. 1 is top isometric view, FIG. 1A is a bottom isometric view of a steerable sheath catheter 10 according to a first embodiment, and FIG. 2 is an exploded view of the steerable sheath catheter 10 of FIG. 1. In the embodiment of FIG. 1, the steerable sheath catheter 10 includes a steerable sheath handle 20 (which may also be described as a control handle) and a catheter section including a sheath 90 that may be positioned in the body vasculature. The steerable sheath handle 20 comprises a handle housing 21 having a proximal end 12 and distal end 14, and an actuator portion or knob assembly 74/80 at the distal end 14. The handle housing 21 includes a port 52 connected to a tube 54 which in turn is connected to a three-way stopcock 56 for introduction of fluids into the catheter 10, and a hemostatic valve 50 also at the proximal end 12.

Details of the components of the steerable sheath catheter 10 will now be described with reference to the exploded view of FIG. 2 and the details shown in FIGS. 3-9A. The handle housing 21 includes a top/upper housing section 22 and a bottom/lower housing section 24 which enclose the internal components. The internal components include the hemostatic valve 50 and port 52, right guide 32 and left guide 42, threaded drive tube 60, guide tube 70, front knob section 74, dampening ring 72, and the sheath 90 (proximal portion). The sheath 90 includes a pair of pull or guide wires 92a, 92b which are threaded through respective holes 93a, 93b into the internal passage within the sheath 90, the guide wires 92a, 92b extending the length of the sheath 90 and attached to a tip 91 (see FIG. 1). Thus the sheath 90 may comprise a body section proximal of the tip 91. The guide wire 92a is coupled or secured to the right guide 32 via a crimp connector 39a and the guide wire 92b is coupled or secured to the left guide 42 via the crimp connector 49a (see FIG. 3). The top and bottom housing sections 22, 24 are each provided with flexible/grippable overmold sections 26, 28 to provide a better gripping surface.

Figure 3:
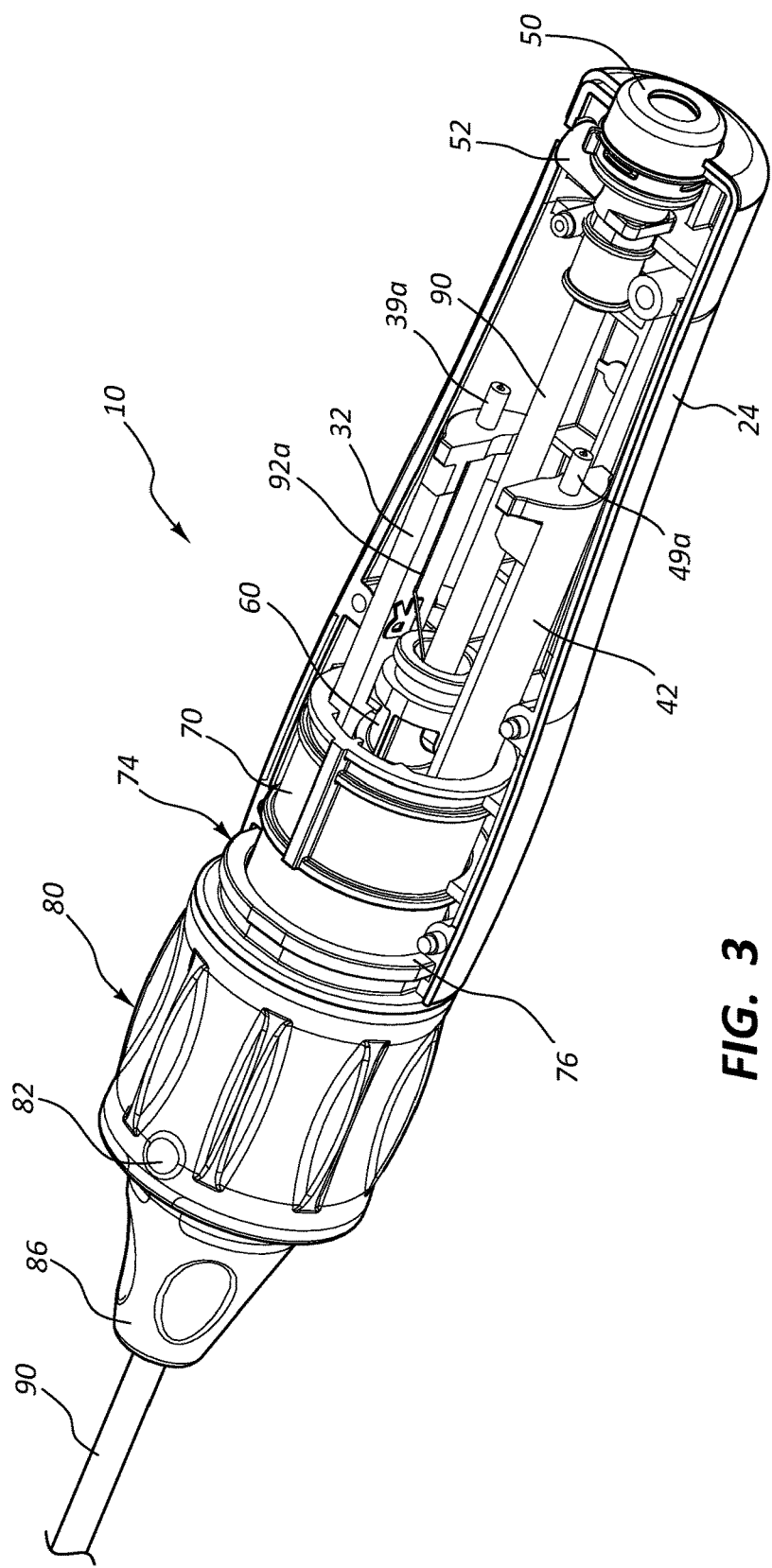
FIGS. 3-5 are isometric views of the top of the sheath handle of FIG. 1 with its top cover removed, wherein in FIG. 3 the guides are in the neutral position, in FIG. 4 the guides are in the left guide retracted position, and in FIG. 5 the guides are in the right guide retracted position.
Figure 4:
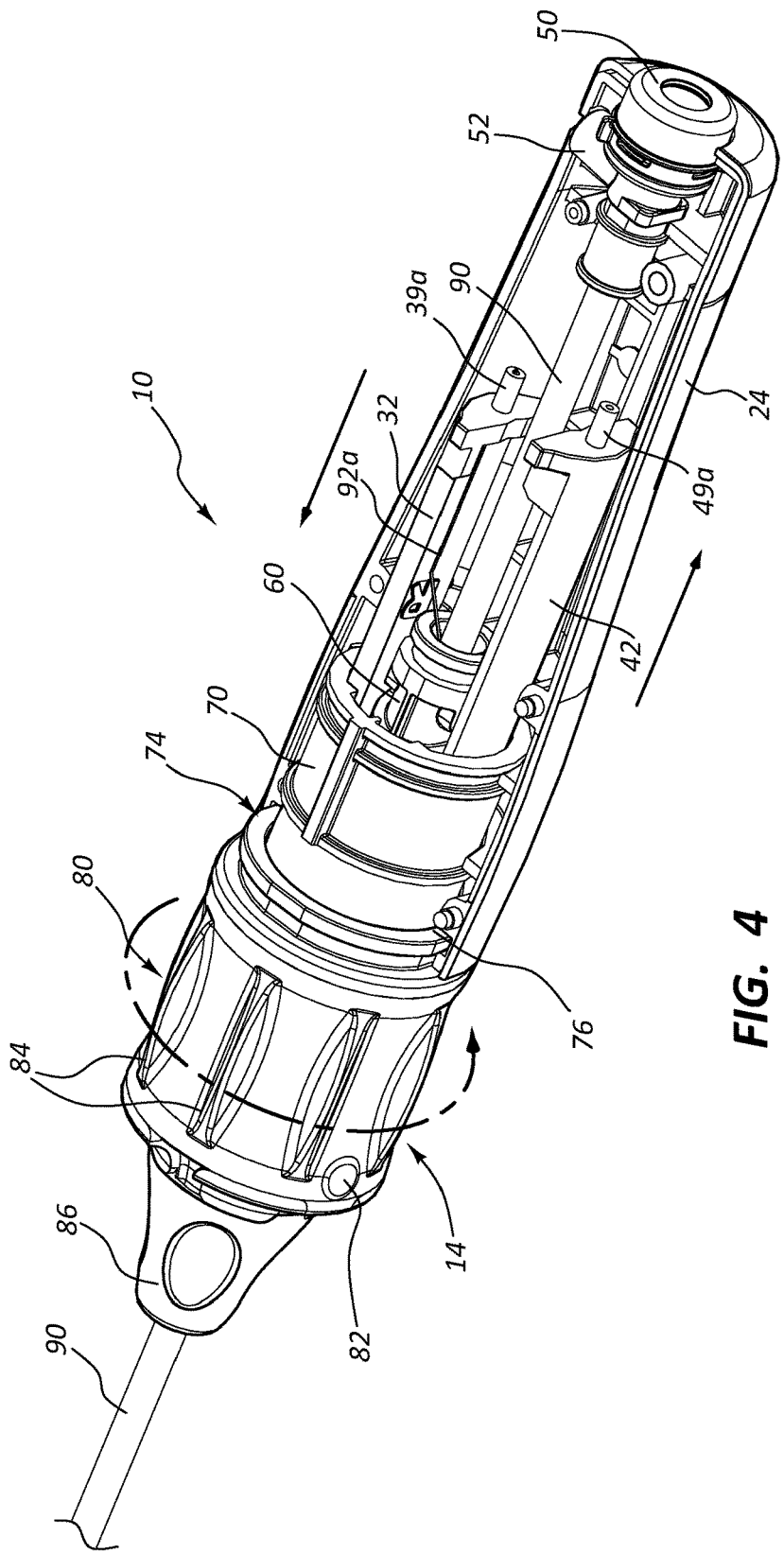
Figure 5:
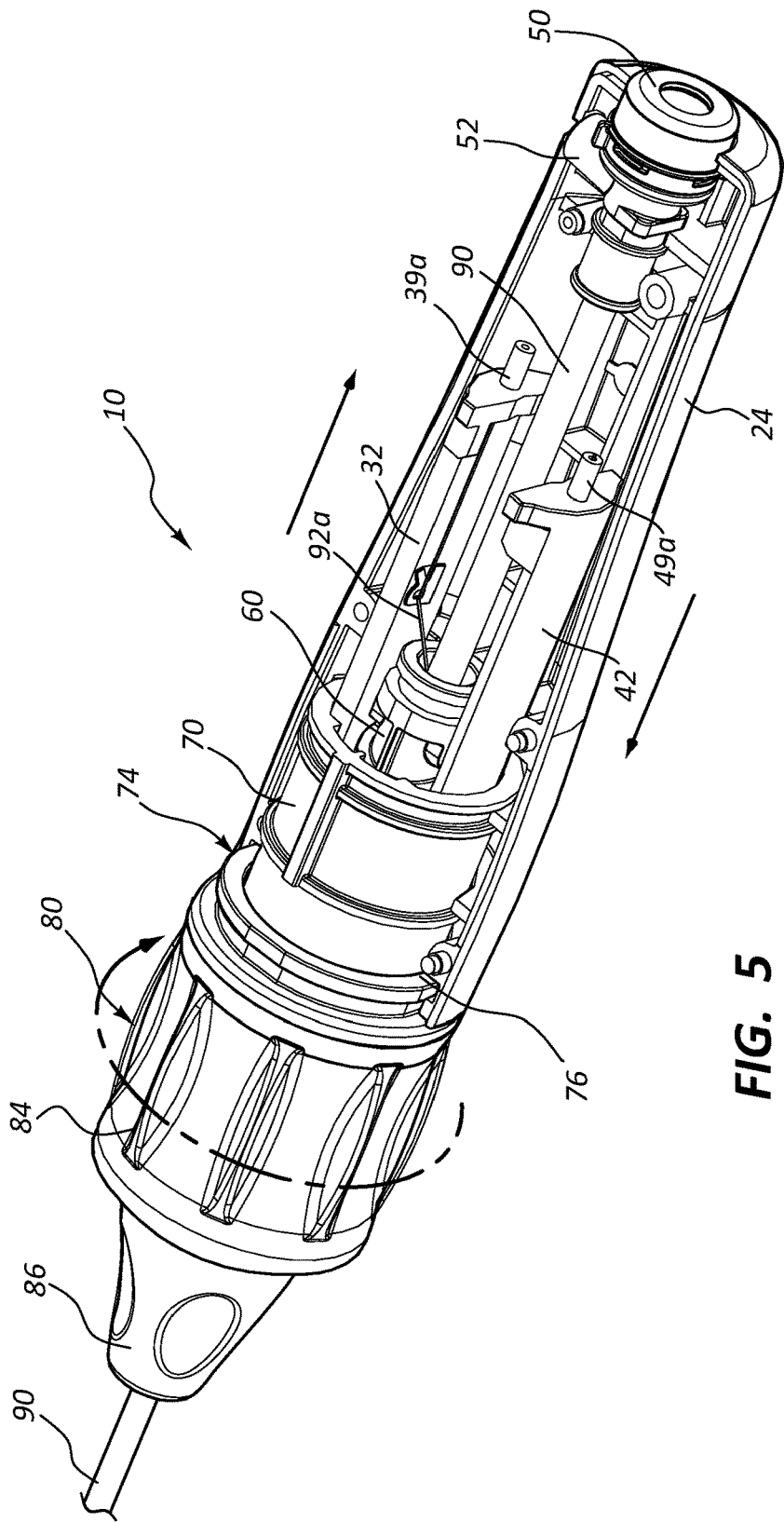

The top and bottom housing sections 22, 24 are provided with internal ribs and support portions for supporting and securing the various components in the desired positions and to allow the desired rotational capabilities of certain components. The right and left guides 32, 42 are disposed around the threaded drive tube 60 and are supported within the handle housing 21 to slide longitudinally as shown in FIGS. 3-5. The threaded drive tube 60 includes left hand thread 64 and right hand thread 65 disposed on the central tubular section 61. The threaded drive tube 60 also includes an end section 66 with a shoulder to seat on a corresponding ledge within the housing sections 22, 24. At its distal end, the threaded drive tube 60 includes a flange 62 having notches 63b, 63b (see FIGS. 6, 6A). The notches 63a, 63b are coupled to and mate with corresponding tabs 73a, 73b (see FIG. 2A) at the distal end of the front knob section 74. When assembled, the right and left guides 32, 42 are secured around the threaded drive tube 60 and inserted into/within the guide tube 70. The dampening ring 72 may comprise a compressible or resilient material, such as a foam or other material. The dampening ring 72 may provide a resilient cushion to account for tolerance or slack between other components of the assembly to facilitate a smooth feel during operation.

The right guide 32 includes a central section 33, a front section 34 and a rear section 37 as shown in FIG. 7. The guide wire 92a passes through wire hole 39 in the rear section 37 where it is secured by the crimp connector 39a (see FIG. 3). The front section 34, details of which are shown in the enlarged detail of FIG. 9A, includes right hand threads 35, 36 for engaging the corresponding right hand thread 65 in the threaded drive tube 60. A tab 38 is disposed on an inner surface of the front section 34 providing the tactile feedback as will be described further below.

Similarly, the left guide 42, details of which are shown in FIG. 8, includes a central section 43, a front section 44 and a rear section 47. The guide wire 92b passes through a wire hole 49 in the rear section 47 where it is secured by the crimp connector 49a (see FIG. 3). The front section 44 includes left hand threads 45, 46 for engaging the corresponding left hand thread 64 in the threaded drive tube 60. A tab 48 is disposed on an inner surface of the front section 44 providing the tactile feedback as will be described further below.

Figure 9A:
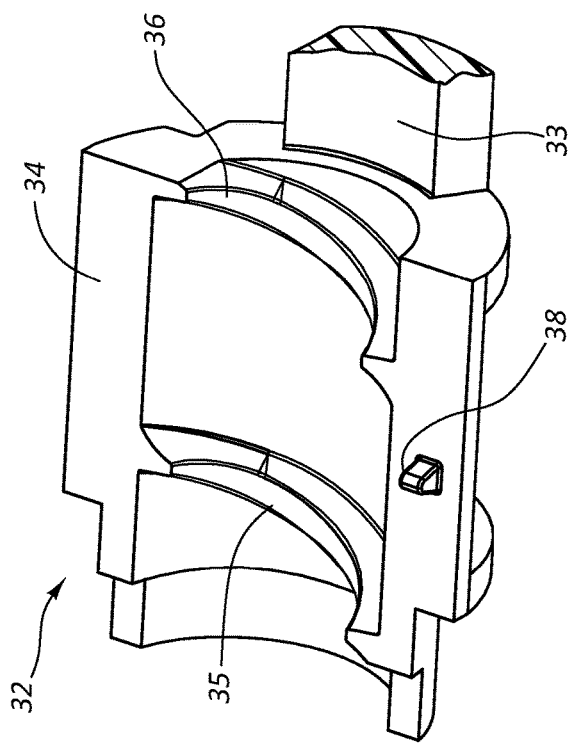
FIG. 9A is a detailed view of a portion of the right guide of FIG. 7.
Figure 9B:
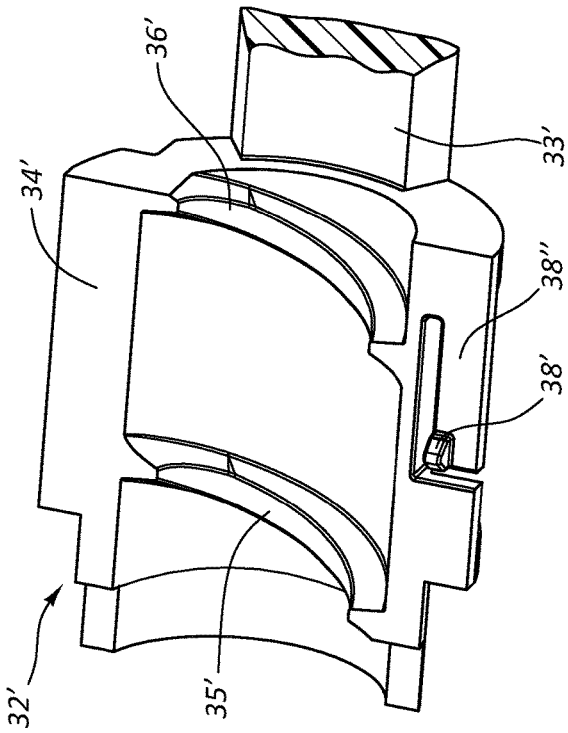
FIG. 9B is a detailed view of an alternative design of a right guide.

FIG. 9B is an alternative embodiment of a right guide 32' showing a central section 33', a front section 34', and right hand threads 35', 36'. The right guide 32' is analogous to the right guide 32 of FIG. 9A. Right guide 32' further includes a tab 38'. The tab 38' may function in an analogous manner to the tab 38 of the right guide 32 of FIG. 9A. By comparison with the embodiment of FIG. 9A, the right guide 32' comprises a cut-away portion in communication with the tab 38', creating a cantilever arm 38'' coupled to the tab 38'. This cantilever arm 38'' may act as a cantilever spring, and may partially deflect when the tab 38' contacts another tab (such as a tab on a left guide). This may provide compliance to the system, facilitate smooth operation, increase the perception of tactile feedback, and so forth. It is within the scope of this disclosure to provide cantilever arms in connection with tabs on both right and left guides of an assembly, or on only a single guide.

The front knob section 74 includes a tip portion 78 on the distal end thereof, a central body section 75 and a collar flange 76 on the front or proximal end, the collar flange seating within a notch within the housing sections 22, 24. A knob section 80 (of more flexible plastic or rubber overmold, for example) is disposed about the central portion 75 of the front knob section 74 and over the tip portion 78 to provide a more flexible and superior gripping surface for grasping and manipulating the unit. The knob section 80 includes gripping ribs 84, a position button or thumb marker 82, and a tip section 86 that surrounds the tip portion 78 of the front knob section 74.

As shown in FIGS. 3-5, rotation of the knob assembly 74/80 serves to rotate the internal threaded tube 60 (as previously described, the distal flange 62 with its notches 63a, 63b engage the tabs 73a, 73b within the front knob section 74, thus rotation of the knob assembly 74/80 serves to rotate the threaded drive tube 60). Rotation of the threaded drive tube 60 serves to longitudinally translate the left and right guides 42, 32 in opposite directions via operation of the threaded connections between the elements. FIG. 3 illustrates the right and left guides 32, 42 in a neutral position. FIG. 4 illustrates the left guide in a retracted position, longitudinally translated to a more proximal position thus pulling on the guide wire 92b while the right guide 32 has been translated to a more distal position extending the guide wire 92a forward or to a more distal location, thus manipulating the tip 91 to the left. FIG. 5 illustrates the right guide 32 in a retracted position, longitudinally translated to a more proximal position pulling on the guide wire 92a whereas the left guide 42 was translated to a more distal position moving the guide wire 92b to a more distal location, thus manipulating the tip 91 to the right. Thus the steerable sheath handle 20 provides for bi-directional deflection of the tip 91.

The threads 64, 65 on the threaded drive tube 60 and the threads 35, 36 in the right guide 32 and threads 45, 46 in the left guide 42 are provided with a suitable pitch to produce a desired longitudinal translation via manipulation of the steerable sheath corresponding to a desired rotation of the knob assembly 74/80. The device may be provided with stops such as when the actuation knob is rotated, for example, clockwise by a desired amount, the left guide 42 will reach a stop point such as against a stop along the inner distal end of the front knob section 74 and similarly if rotated in a counterclockwise direction, the right guide 32 will reach a stop within the front knob section 74 providing a tactile feedback to the user.

Tactile features are also provided on the external portions of the sheath handle 20. The grip surface 26 on top of the upper housing section 22 includes a tactile feature 27 that may be felt by the practitioner to provide feedback of the top center position of the sheath handle 20. The grip surface 28 on the bottom housing section 24 may include a similar tactile feature 29. The knob section 80 may also be provided with a button 82 that may be felt by the user, thus providing feedback to the user that the control position of the unit (as controlled by the knob assembly 74/80) is at the neutral position such as shown in FIG. 3. As previously described, the relative pitch of the threads 64, 65, 35, 36, 45, 46 may be designed such that a single rotation left or right is less than a maximum of 360° from the neutral position shown in FIG. 3 to provide the maximum amount of travel of the right and left guides 32, 42.

The button 82, though useful, may not provide sufficient or even entirely accurate feedback. The user may manipulate the steerable sheath handle 20 without contacting the button 82 and thus will not encounter any feedback of the control position thereby. Moreover, it may be desired to provide finer control for the user whereby the knob assembly 74/80 is rotatable more than a total of 360° in each direction. Where the total travel allowed is controlled by a rotation greater than 360° in either direction, it may be difficult for the user to determine when the knob assembly 74/80 is at the "zero" position with the right and left guides 32, 42 at the neutral position as in FIG. 3 or at some other position. Thus the steerable sheath catheter 10 is provided with a tactile indicator comprising the tabs 38, 48 which contact each other when passing in either direction past the neutral center point of the control as shown diagrammatically in FIG. 10. As the tabs 38, 48 pass by and contact each other, a tactile feedback and/or "click" sound (thus tactile and/or audible feedback) provides an indication or confirmation to the user that the device has reached the neutral position, thus the user can feel (and/or hear) the position and does not have to look at a display screen or down at the sheath handle 20 to confirm that the device is at the actual center point or neutral position. The tactile feedback mechanism may be used for devices rotatable less than 360° in either direction, but may be particularly useful for a device configured such that the knob assembly 74/80 turns more than one rotation in either direction for providing finer/smaller and more precise adjustments to the tip 91. It is noted that the knob indicator/button 82 cannot indicate neutral position for a device configured such that the knob assembly 74/80 turns more than one rotation in either direction.

Figure 11:
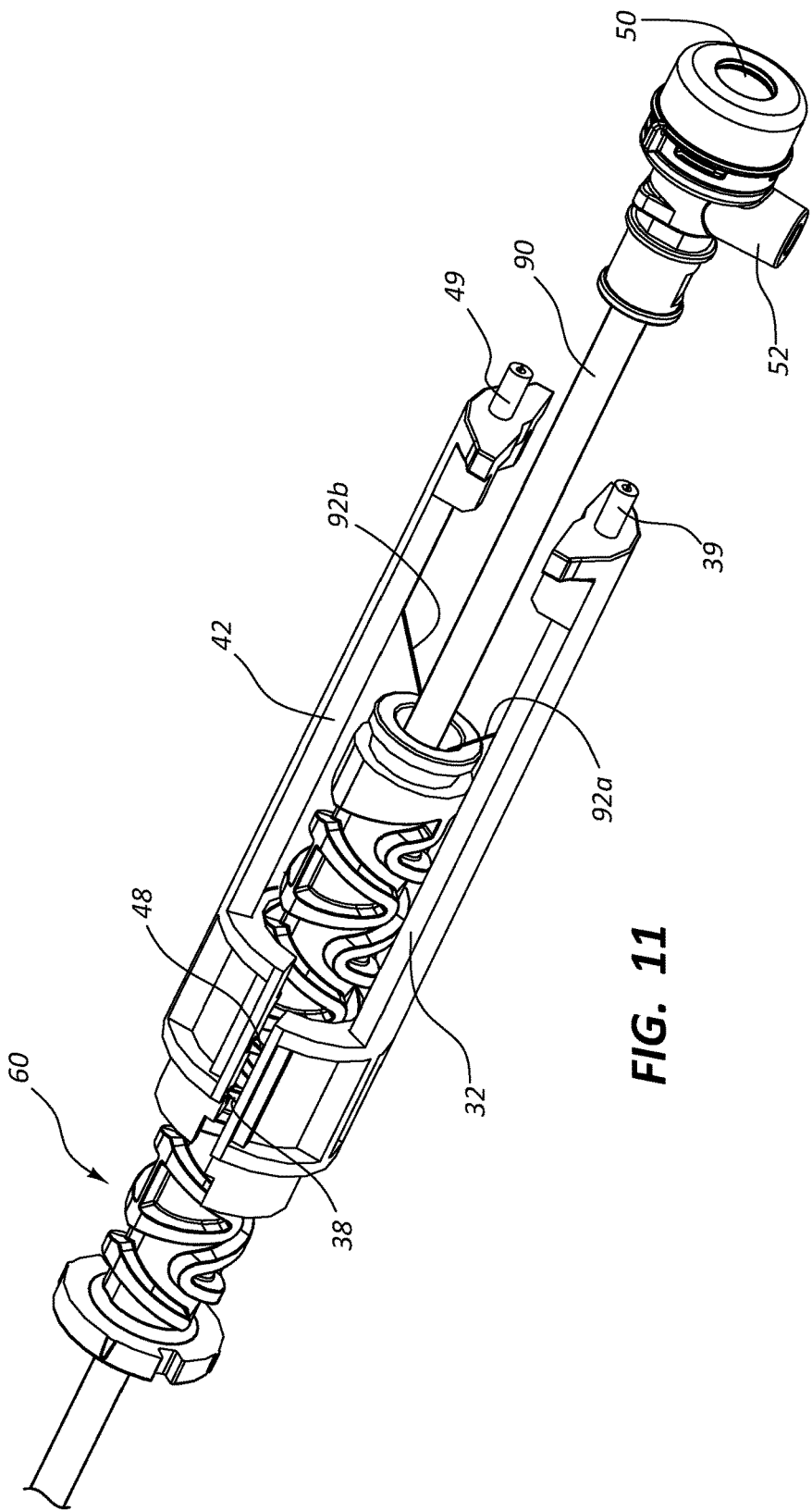
FIGS. 11-13 are isometric views of the bottom of the sheath handle of FIG. 1 with its covers removed, wherein in FIG. 13 the guides are in the neutral position, in FIG. 12 the guides are in the left guide retracted position, and in FIG. 11 the guides are in the right guide retracted position.
Figure 12:
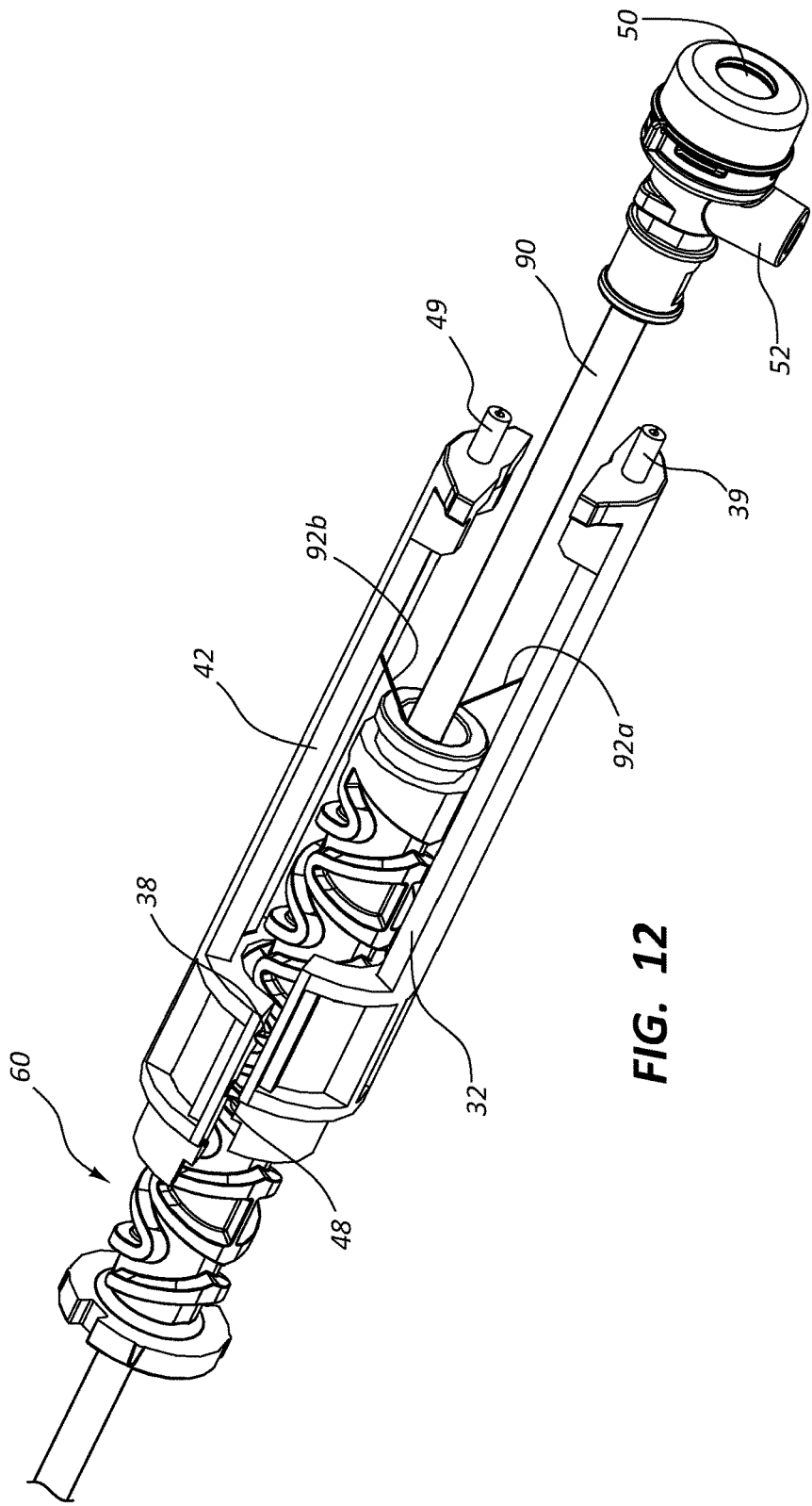
Figure 13:
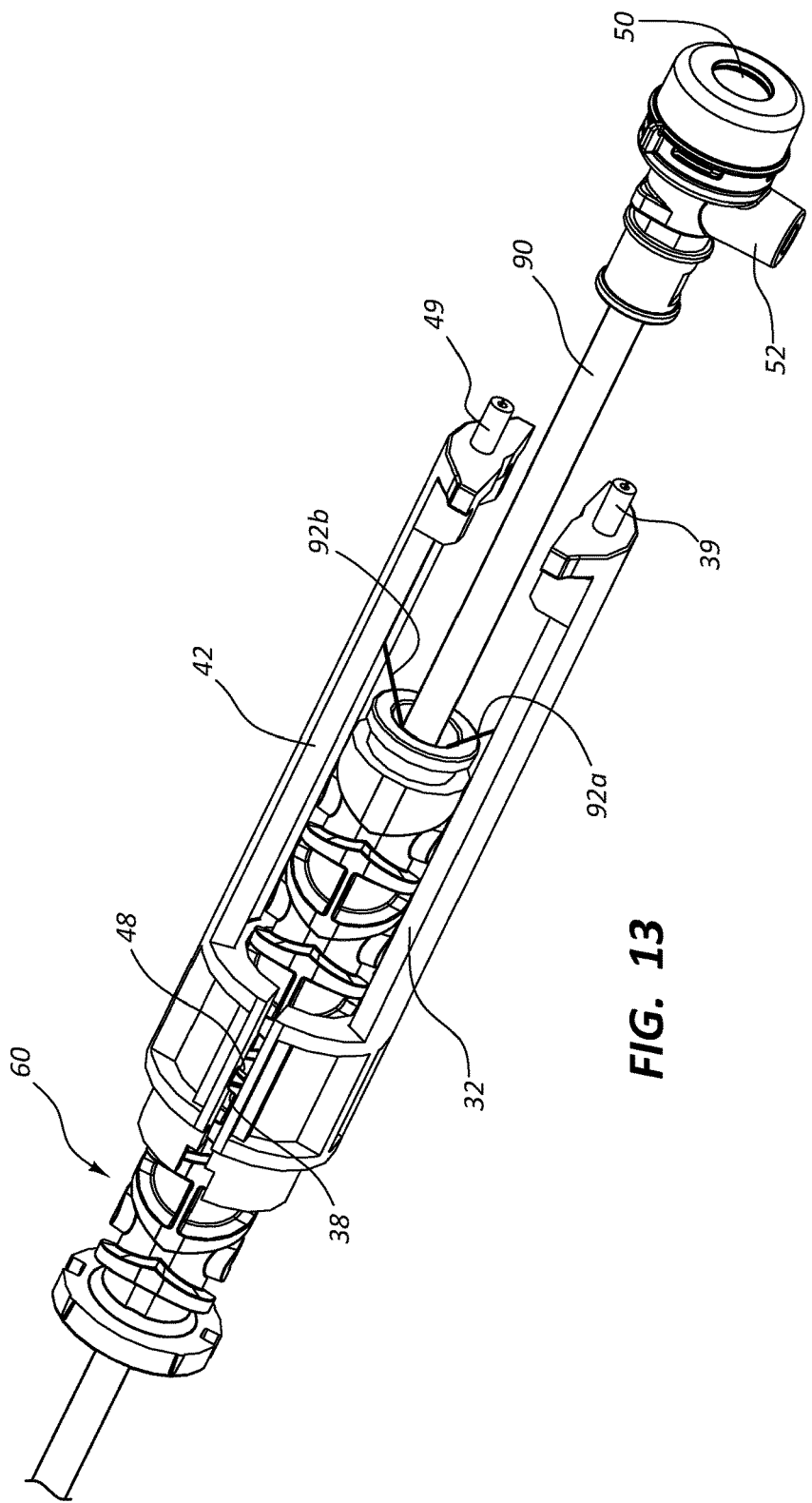

FIGS. 11-13 illustrate the sheath handle 20 with the outer housing removed and showing primarily only the right and left guides 32, 42, the view being from the bottom thereby showing the relative positions of the tabs 38, 48 for the various positions. Specifically, FIG. 11 shows the left guide 42 in the retracted or proximal position pulling on the guide wire 92b, FIG. 12 shows the right guide in the retracted position more proximal to the proximal end, and FIG. 13 illustrates the right and left guides 32, 42 in the center point or neutral position whereby the tabs 38, 48 are in a generally contacting condition.

Figure 14:
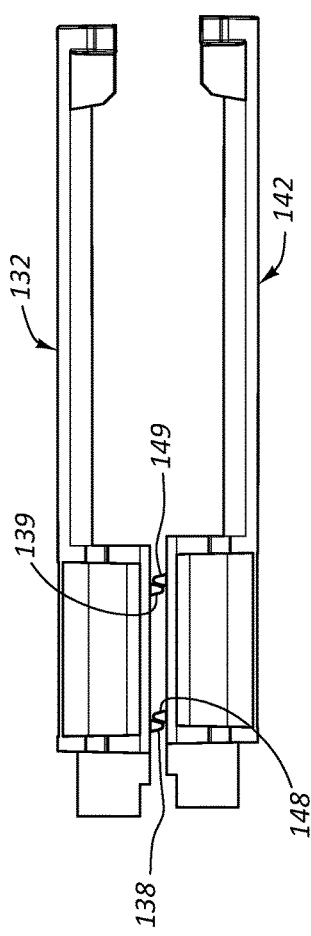
FIGS. 14-16 are diagrammatic top views of an alternative embodiment for a steerable sheath handle having multiple tactile feedback positions.
Figure 15:
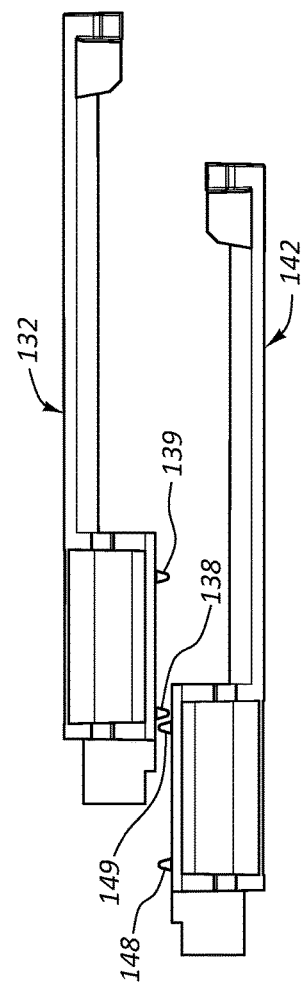
Figure 16:
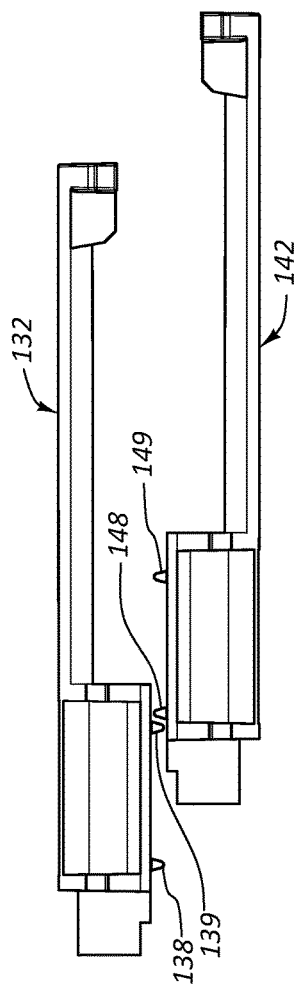

In another example, the sheath handle 20 may include multiple tactile indicators indicating different tip adjustment positions for the steerable sheath catheter 10. FIGS. 14-16 diagrammatically illustrate a configuration providing three tactile indicators. FIG. 14 illustrates right and left guides 132, 142 in the center point or neutral position. The right guide 132 includes a first tab 138 and a second tab 139 and the left guide 142 includes a first tab 148 and a second tab 149. In the neutral position as in FIG. 14, the first tab 138 on the right guide 132 lines up and contacts against the first tab 148 on the left guide 142 and the second tab 139 on the right guide 132 lines up and contacts the second tab 149 of left guide 142. As the right and left guides 132, 142 are actuated and moved in either direction, the tab contacting combinations provide a tactile feedback to the practitioner of the center position. As shown in FIG. 15, as the left guide 142 is moved forward and the right guide 132 is moved rearward, the first tab 138 on the right guide 132 contacts the second tab 149 on the left guide 142 providing a tactile feedback indication of a position corresponding to, for example, a right bend to the catheter tip 91 of 90°. FIG. 16 illustrates the right guide 132 moved forward and the left guide 142 moved rearward, to a position whereby the second tab 139 in the right guide 132 contacts the first tab 148 in the left guide 142 providing a tactile feedback of a third position for example that the tip is bent at an angle to the left of for example 90°.

It is noted that the front sections of the guides 132, 142 are somewhat longer than the front sections 34, 44 of the prior embodiment so as to accommodate separation as between first and second tabs 138, 139 (or 148, 149) on the same front section. Additional tabs may be provided to provide additional tactile feedback positions. It is further noted in the examples of FIGS. 14-16 that the center point/neutral position indication will have two sets of tabs contacting (see FIG. 14) which may provide a greater or larger tactile feedback magnitude in comparison to the single tab pair contacts at the 90° positions of FIGS. 15 and 16.

In operation, the steerable sheath handle 20 may be used for controlling or manipulating the bendable tip 91 of the catheter sheath 90 in a desired direction and providing a feedback (i.e., tactile feedback that may be felt by the user and/or audible feedback) as the device actuator moves the steering mechanism past a desired angular position, such as the neutral position and/or other positions.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

What is claimed is:

1. A catheter system, comprising:
   a handle section;
   an actuator operably coupled to the handle section;
   a catheter coupled to the handle section, the catheter comprising a body section extending from the handle section and a tip section coupled to a distal end of the body section;
   the tip section of the catheter operably coupled to the actuator such that displacement of the actuator with respect to the handle section manipulates the position of the tip section of the catheter with respect to the body section of the catheter,
   wherein the tip section of the catheter is operably coupled to the actuator by a drive mechanism comprising a right guide and a left guide; and
   a feedback mechanism configured to provide feedback to a user regarding the position of the tip section of the catheter with respect to the body section of the catheter, wherein the feedback mechanism comprises: a first tab disposed on the right guide and a second tab disposed on the left guide, wherein the first and second tabs contact each other as the right and left guides are longitudinally displaced, thus providing the feedback.

2. The catheter system of claim 1, wherein the feedback mechanism provides tactile feedback.

3. The catheter system of claim 1, wherein the feedback mechanism provides audible feedback.

4. The catheter system of claim 1, wherein the drive mechanism further comprises:
   a right guide wire and a left guide wire coupled to the tip section of the catheter;
   wherein the right guide is connected to the right guide wire and the left guide is connected to the left guide wire; and
   a threaded drive tube having right and left threads operably connected to respective threads in the right and left guides, the threaded drive tube coupled to the actuator such that upon rotation of the threaded drive tube by the actuator, the left and right guides are longitudinally translated in opposite directions.

5. The catheter system of claim 4, wherein the first and second tabs contact each other when the tip section of the catheter is in a neutral position with respect to the body section of the catheter.

6. The catheter system of claim 5, wherein the neutral position corresponds to longitudinal alignment of the tip section of the catheter and the body section of the catheter.

7. The catheter system of claim 5, wherein the feedback mechanism further comprising a third tab configured to provide feedback to a user at a position other than the neutral position.

8. The catheter system of claim 4, wherein at least one of the first and second tabs is disposed on a cantilever arm.

9. A steerable sheath catheter system, comprising:
   a handle section;
   an actuator disposed in or on the handle section;
   a sheath that is insertable into a body vascular and having a proximal end and a distal end, the sheath being connected at its proximal end to the handle section;
   a tip section disposed at a distal end of the sheath;
   first and second guide wires threaded through the sheath and connected to the tip section;
   a drive mechanism disposed in the handle section operable for displacing the first and second guide wires to manipulate the tip section between a neutral position and a selected left position and between the neutral position and a selected right position;
   a feedback mechanism operable to provide tactile feedback to the user, wherein the feedback mechanism comprises multiple tactile indicators indicating different tip positions.

10. The steerable sheath catheter system of claim 9, wherein the drive mechanism comprises:
    a right guide connected to the first guide wire and a left guide connected to the second guide wire; and
    a threaded drive tube having right and left threads operably connected to respective threads in the right and left guides, wherein upon rotation of the threaded drive tube by the actuator, the left and right guides are longitudinally translated in opposite directions.

11. The steerable sheath catheter system of claim 10, further comprising a first tab disposed on the right guide and a second tab disposed on the left guide, wherein the first and second tabs contact each other as the right and left guides pass the neutral position thereby providing the tactile feedback.

12. The steerable sheath catheter system of claim 9, wherein rotation of the actuator with respect to the handle section manipulates the tip section between the neutral position and a selected left position and between the neutral position and a selected right position.

13. The steerable sheath catheter system of claim 12, wherein the actuator is configured to rotate more than 360° with respect to the handle when manipulating the tip section between the neutral position and at least one of the selected left position and the selected right position.

14. The steerable sheath catheter system of claim 13, wherein at least one of the selected left position and the selected right position comprises a maximum left displacement of the tip or a maximum right displacement of the tip, respectively.

15. The steerable sheath catheter system of claim 9, wherein the feedback mechanism further provides audible feedback to the user.

16. A method of displacing a steerable catheter tip comprising:
    displacing a first guide member with respect to a second guide member, the first and second guide members operably coupled to a tip section of the catheter such that displacement of the first and second guide members manipulates the position of the tip section of the catheter; and
    displacing a first tab with respect to a second tab such that contact between the first and second tabs provides feedback to a user, wherein the first tab is coupled to the first guide and the second tab is coupled to the second guide.

17. The method of claim 16, wherein the feedback comprises tactile feedback.

18. The method of claim 16, wherein the feedback comprises audible feedback.

19. The method of claim 16, further comprising displacing a third tab such that the relative position of the third tab with respect to at least one of the first tab and the second tab provides secondary feedback to a user.

20. The method of claim 19, wherein contact between the third tab and a fourth tab provides the secondary feedback.

21. A method of using a steerable sheath catheter having a control handle during a medical procedure on a patient, comprising the steps of:
    positioning a sheath into a body vascular of the patient;
    actuating a control mechanism on the control handle of the catheter to selectively deflect a tip section of the catheter;
    providing tactile feedback that is felt by the user as the control mechanism passes a neutral position while deflecting the tip section;
    provide tactile feedback to the user as the control mechanism passes a position other than the neutral position.

* * * * *